United States Patent [19]

Nambu et al.

[11] Patent Number: 5,412,562
[45] Date of Patent: May 2, 1995

[54] COMPUTERIZED TOMOGRAPHIC IMAGING METHOD AND SYSTEM FOR ACQUIRING CT IMAGE DATA BY HELICAL DYNAMIC SCANNING

[75] Inventors: Kyojiro Nambu; Tatsuya Ban, both of Tochigiken, Japan

[73] Assignee: Kabushiki Kaisha Toshiba, Kanagawa, Japan

[21] Appl. No.: 42,274

[22] Filed: Apr. 2, 1993

[30] Foreign Application Priority Data

Apr. 2, 1992 [JP] Japan .................................. 4-080858
Jul. 16, 1992 [JP] Japan .................................. 4-189340

[51] Int. Cl.$^6$ ...................... G06F 15/00; G01N 23/00; A61B 5/02
[52] U.S. Cl. .................. 364/413.15; 364/413.17; 378/10; 128/678
[58] Field of Search ................ 364/413.15, 413.17, 364/413.18, 413.21; 378/10, 19, 17; 128/678

[56] References Cited

U.S. PATENT DOCUMENTS

| | | | |
|---|---|---|---|
| 4,630,202 | 12/1986 | Mori .................. | 364/413.15 |
| 4,994,965 | 2/1991 | Crawford et al. ............. | 364/413.15 |
| 5,073,911 | 12/1991 | Ozaki et al. ............. | 578/17 |
| 5,262,946 | 11/1993 | Heuscher ................. | 364/413.18 |

Primary Examiner—Gail O. Hayes
Assistant Examiner—Khai Tran
Attorney, Agent, or Firm—Finnegan, Henderson, Farabow, Garrett & Dunner

[57] ABSTRACT

In a helical dyamic scanning X-ray CT imaging system, an X-ray source is continuously moved on the same orbit during plural helical scanning operations by controlling a projection direction and a translation of a biological body that is to be examined medically. The helical dynamic scanning X-ray CT imaging system includes a system for helically scanning the biological body as the body is translated along a Z-axis to obtain projection image data of the body along the helically scanned path. Radiation is projected from a radiation source to the biological body being translated along the Z-direction as the radiation source simultaneously moves around the translated biological body. The helical scanning process is carried out during at least first and second helical scanning operations while detecting a radiation angle of the radiation source being detected. The helical scanning process is controlled in such a manner that a first projection angle of the radiation source at a first starting position of the first helical scanning operation is coincident with a second projection angle of the radiation source at a second starting position of the second helical scanning operation.

8 Claims, 11 Drawing Sheets $A_1-A_0$        $A_2-A_0$        $A_3-A_0$

TIME LAPSE $t_{A1}-t_0$    TIME LAPSE $t_{A2}-t_0$    TIME LAPSE $t_{A3}-t_0$

FUNCTIONAL IMAGE

RING OF DETECTOR

COMPUTERIZED TOMOGRAPHIC IMAGING METHOD AND SYSTEM FOR ACQUIRING CT IMAGE DATA BY HELICAL DYNAMIC SCANNING

BACKGROUND OF THE INVENTION

1. Field of the Invention

The present invention generally relates to a computerized tomographic (CT) imaging method and a CT imaging system capable of helically dynamic-scanning a biological body under medical examination to obtain a CT image thereof. More specifically, the present invention is directed to such CT imaging method/system capable of helically scanning the same biological body for several times, while a contrast medium is injected into this biological body, thereby obtaining a contrast image thereof without any artifact.

2. Description of the Prior Art

Various types of CT (computerized tomographic) imaging methods/systems have been developed in the medical electronic fields, for instance, X-ray CT imaging systems, single photon emission CT (SPECT) imaging systems, and position emission tomography (PET) imaging systems.

In particular, a so-called "helical scanning" type X-ray CT imaging apparatus/system has also been developed and marketed in this field. A typical "helical scanning" type X-ray CT imaging apparatus is known from, for instance, U.S. Pat. No. 4,630,202 to Isei Mori, entitled "COMPUTERIZED TOMOGRAPHIC APPARATUS UTILIZING A RADIATION SOURCE", patented on Dec. 16, 1986. In this helical scanning type X-ray CT apparatus, while a biological body under medical examination is translated with respect to an X-ray source and an X-ray detector, a predetermined portion of this biological body is scanned as a data acquisition region by projecting X-ray beams through this portion to the X-ray detector in such a way that the X-ray source is continuously moved along a helical orbit around this biological body. For a further description of helical scanning techniques, see the above-described Mori U.S. Patent specification.

Helical scanning type CT imaging method/system defined in the improvement of the present invention provides improvement over those described above. However, to facilitate understanding of the present invention, one conventional helical scanning type X-ray CT imaging system will now be described.

Referring now to FIGS. 1 to 7, the typical helical scanning operation and the artifact problem caused in one conventional X-ray CT imaging system will be explained. FIG. 1 schematically shows an overall arrangement of the conventional X-ray CT imaging system. FIGS. 2A and 2B schematically represent helical dynamic scanning operation timing charts of the conventional X-ray CT imaging system. FIGS. 3A and 3B illustrate angiograms and a functional image acquired by the conventional X-ray CT imaging system. FIG. 4 schematically indicates a detector array of the conventional nutate-rotate type X-ray CT imaging system. FIG. 5 schematically indicates a basic structure of this conventional helical dynamic scanning type X-ray CT system. FIGS. 6A, 6B, 6C and 7 schematically show the couch position/X-ray source angle/helical scanning orbit of the conventional helical scanning type X-ray CT imaging system.

Referring back to FIG. 1, the overall arrangement of the conventional helical scanning type X-ray CT imaging system will now be described.

In FIG. 1, a pair of X-ray source 41 and X-ray detector 31 are positioned within a gantry 2 in such a manner that the X-ray source 41 and the X-ray detector 31 are mutually rotatable and positioned opposite to each other with respect to a biological body 10 under medical examination laid on a couch 43. The couch 43, i.e., the biological body 10 such as a patient is translated along a direction indicated by symbol "Z" (namely, longitudinal direction of the biological body) by driving a couch servomotor 40. A present position of this couch 43 is sensed by a couch position sensor 45.

The X-ray source 41 and the X-ray detector 31 are relatively rotatable by driving a detector servomotor 20 along a rotation direction "R". A rotation angle of this X-ray detector 31 is sensed by an angular sensor 30 to produce angle data "$\theta$". A data acquisition unit 3 is employed within the gantry 2 to produce helical scanning data.

A main control unit 50 is employed and a clock generator 52 is also employed. In response to clock pulses produced from the clock generator 52, the main control unit 50 mainly supplies control signals to the DAS unit 3, the X-ray detector servomotor 20, the angular sensor 30, the couch servomotor 40, and a computing unit 80. A CT image derived from the computing unit 80 is displayed on a monitor 82.

Referring now to the timing charts shown in FIGS. 2A, 2B and the images indicated in FIGS. 3A and 3B, the conventional helical dynamic scanning operation by the X-ray CT imaging system of FIG. 1 will be described.

In FIG. 2A, an ordinate represents a slice position of the conventional dynamic scanning operation, and an abscissa shows time instants "$t_{A0}$", "$t_{A1}$", - - - , "$t_{B0}$", "$t_{B1}$", - - - , "$t_{02}$". Symbols "$A_0$", "$A_1$". - - - , "$B_0$", "$B_1$", - - - , "$B_2$" represent X-ray images acquired at the above-described time instants "$t_{A0}$", - - - , "$t_{03}$", respectively.

Assuming now that an X-ray contrast medium is injected to the biological body 10 under medical examination at a time instant between the time instant "$t_{B0}$" and the time instant "$t_{A1}$", since two sets of images "$A_0$" and "$B_0$" correspond to images acquired before the injection of the X-ray contrast medium, as shown in FIG. 2B, subtraction images "A1-A0", "B1-B0", "A2-A0", "B2-B0", "A3-A0", and "B3-B0" are formed in the computing unit 80. FIG. 3A schematically shows subtraction images "A1-A0", "A2-A0", and "A3-A0". A functional image may be obtained from these subtraction images "A4-A0", "A2-A0", and "A3-A0" by extracting characteristic values of variations contained in the images and then by indicating the characteristic values as high/low density values. For instance, FIG. 3B schematically shows a peak time image (=functional image) the respective pixels of which are indicated by the high/low density values corresponding to such time instants when the density values of the X-ray contrast become maximum, namely the CT values thereof become maximum. From such a functional image shown in FIG. 3B, it can be easily recognized such a position where the X-ray contrast medium has reached at first.

As previously described, when the helical scanning operation would be repeatedly performed for the same slice portions of the biological body 10, while the X-ray contrast medium is injected into this biological body (namely, the helical dynamic scanning operation is carried out), an artifact would be practically induced in the subtraction images of FIG. 3A.

APPEARANCE OF ARTIFACT IN SUBTRACTION IMAGE

The reason why such an artifact would appear in the subtraction image will now be described more in detail.

In the basic structure of the conventional helical scanning type X-ray CT imaging system shown in FIG. 5, it is now assumed that the helical dynamic scanning operation would be carried out. As shown in FIG. 5, the X-ray source 41 is rotated at a constant speed on an orbit 42, and a position thereof is indicated by an angle "$\theta$". This angle "$\theta$" is detectable by the angular sensor 30 of FIG. 1 as angle data. The couch 43 on which the biological body 10 is laid, is translatable along the Z-direction, i.e., the longitudinal direction of the biological body 10.

A relationship between the position of the X-ray source 41, i.e., the setting angle of the X-ray source 41, and the time lapse "t" is indicated in FIG. 6A. Another relationship between the position of the couch 43 and the time lapse "t" is shown in graphic FIG. 6B. A range defined by $A \leq Z \leq B$ in the ordinate of the graphic region 6B corresponds to a range for acquiring X-ray image data. X-ray pulses are projected from the X-ray source 41 to the biological body 10 and penetrated through this biological body 10 laid on the couch 43, and then detected by the X-ray detector 31, while the couch 43 is present at least within this range defined by $A \leq Z \leq B$. During this range, the translation speed of the couch 43 on which the biological body 10 is laid is constant under control of the couch servomotor 40 and the main control unit 50. An X-ray contrast medium (not shown in detail) is injected into the biological body 10 at a preselected timing. As indicated in shown in FIG. 6C, the translation of this couch 43 is repeatedly performed like a first X-ray helical scanning operation and a second helical X-ray scanning operation. Since the helical dynamic scanning operation is executed in the X-ray CT imaging system of FIG. 1, a time instant when the present position of the couch 43 "Z" becomes equal to "Z" ($Z=z$), corresponds to "$t_{z1}$" during the first X-ray helical scanning operation, and also to "$t_{z2}$" during the second X-ray helical scanning operation. It should be noted that the present position of the X-ray source 41 at this first time instant "$t_{z1}$" during the first helical scanning operation corresponds to "$\theta_{tz1}$" (see FIG. 6A), whereas the present position of the X-ray source 41 at the second repeating time instant "$t_{z2}$" during the second helical scanning operation corresponds to "$\theta_{tz2}$" (also see FIG. $\beta$A), and as apparent from FIG. 6A, the first X-ray source position "$\theta_{tz1}$" is not equal to the second X-ray source position "$\theta_{tz2}$" (namely $\theta_{tz1} \neq \theta_{tz2}$).

As described above, if the first position "$\theta_{tz1}$" of the X-ray source 41 would not be equal to the second position "$\theta_{tz2}$" thereof at the same slice position $Z=z$ of the biological body 10, there is a difference in X-ray scanned images acquired during the first and second helical scanning operations, which is not caused by an X-ray contrast medium.

The reason why such a difference happens to appear in a subtraction image will now be analyzed as follows. When a consideration is made of the CT images at one slice position "z", the biological body 10 is actually scanned at the first slice position "$z_1$" during the first helical scanning operation under such a condition that the X-ray pulses are actually projected from the X-ray source 41 only at the angle "$\theta_{tz1}$". In other words, this X-ray projection data is not actually acquired while the X-ray source 41 is rotated by 360° at this first slice position "$z_1$" in order to reconstruct one CT image of this slice portion of the biological body 10. Therefore, according to the conventional helical scanning type X-ray CT imaging system, the interpolation method is utilized so as to reconstruct the desirable X-ray CT image based on other X-ray projection data acquired before and after this first slice position "$z_1$" within a range of rotation angle of 360°.

Subsequently, similar image data acquisition and data reconstruction will be carried out during the second helical scanning operation. Although the second slice position "$z_2$" is identical to the first slice position "$z_1$", the present positions (angles) of the X-ray source 41 are different from each other, namely the first angle "$\theta_{tz1}$" is not equal to the second angle "$\theta_{tz2}$".

That is to say, the X-ray projection data acquired at the second slice position "$z_2$" (=first slice position "$z_1$") are actually different from the above-described X-ray projection data acquired at the first slice position "$z_2$", which will be employed in the data interpolation, namely acquired at the different X-ray source positions (see FIGS. 6A and 6B).

A more detailed explanation about the different data acquisition will now be made.

For instance, to predict projection data from a projection angle (setting angle of X-ray source), of "$\theta$"=0 (see origin of ordinate of graphic region 6A), two sets of actually acquired projection data "$PD_{F1}$" and "$PD_{B1}$" are employed during the first helical scanning operation. The actually acquired projection data "$PD_{F1}$" corresponds to such a projection data from the projection angle "$\theta$"=0 at a slice position of "$z_1 - \Delta YPD_{F1}$". The actually acquired projection data "$PD_{B1}$" corresponds to such a projection data from the same projection angle "$\theta$"=0 at a slice position of "$z_1 + \Delta z_1 DF_{B1}$".

Also, to predict projection data from the projection angle of "$\theta$"=0, two sets of actually acquired projection data "$PD_{F2}$" and "$PD_{B2}$" are employed during the second helical scanning operation, and slice positions thereof are "$z_2 - \Delta z_2 PD_{F2}$" and "$z_2 - \Delta z_2 PD_{B2}$", respectively. Assuming now that $\Delta z_1 PD_{F1} = \Delta z_2 PD_{F2}$ and $\Delta z_1 PD_{B1} = \Delta z_2 PD_{B2}$, the projection data $PD_{F1}$ is equal to the projection data $PD_{F2}$, and also the projection data $PD_{B1}$ is equal to the projection data $PD_{B2}$. As a consequence, the projection data from the direction $\theta = 0$ at the slice position $Z=z$ predicted (interpolated) during the first helical scanning operation should be, in principle, coincident with that predicted during the second helical scanning operation. However, in actual, as represented in FIGS. 6A, 6B and 6C, $\Delta z_1 PD_{F1}$ is not equal to $\Delta z_2 PD_{F2}$, $\Delta z_2 PD_{B1}$ is not equal to $\Delta z PD_{B2}$, the actually acquired projection data $PD_{F1}$ is not identical to the actually acquired projection data $PD_{F2}$, and similarly the actually acquired projection data $PD_{B1}$ is not equal to the projection data $PD_{B2}$. As a result, there is a difference in the interpolation result.

In FIG. 7, the relationship between the projection angle "$\theta$" and the slice position (couch position) "Z" is plotted, where a time instant "t" is understood as variable (simply referred to a "Z—$\theta$ graphic representation"). As apparent from the slice positions "z" of the abscissa, the setting angle (projection angles) "$\theta_{tz1}$" of the X-ray source 41 during the first helical scanning operation is different from the setting angle "$\theta_{tz2}$" of the X-ray source 41 during the second helical scanning operation.

Precisely speaking, in FIG. 7, projection data "$PD_z$" at the slice position "z" along the projection direction "$\theta$" (=0) is predicted by interpolating both of the actually acquired projection data "$PD_{F1}$" and "$PD_{B1}$" during the first helical scanning operation, but by interpolating both of the actually acquired projection data "$PD_{F2}$" and "$PD_{B2}$" which are not equal to "$PD_{F1}$" and "$PD_{B1}$" respectively, during the second helical scanning operation. In other words, although the actually acquired projection data "$PD_{F1}$" and "$PD_{F2}$" are acquired at the same X-ray source positions during the first and second scanning operations, the positions "Z" of the couch 43 are slightly different from each other. Namely, the first helical scanning operation is carried out along orbits 66 and 68, whereas the second helical scanning operation is performed along different orbits 65 and 67. This difference is similarly applied to the actually acquired projection data "$PD_{B1}$" and "$PD_{B2}$". As a consequence, even when the biological body 10 would not be moved on the couch 43, the first and second helical scannings are performed at the same slice position of the biological body 10, but at the different X-ray projection angles "$\theta_{tz1}$", and "$\theta_{tz2}$", so that a subtraction image does not become zero.

When such a difference happens to occur in the image, the following practical problem, i.e., artifact may be caused. For instance, such a helical dynamic scanning operation is carried out in such a manner that the biological body 10 is helically scanned during a first scanning operation, and subsequently, this biological body 10 is again helically scanned after an X-ray contrast medium has been injected thereinto. Under such a series of the helical scanning operation, a certain difference caused by injection of the X-ray contrast medium could be produced between a first X-ray projection image "$I_1$" acquired during the first helical scanning operation and a second X-ray projection image "$I_2$" acquired during the second helical scanning operation. However, actually, other differences than the above-described contrast medium difference appear in the resultant images. Therefore, there are possible risks in appearance of differences that even when the X-ray contrast medium would not be present in the second image "$I_2$", other differences would appear in this second image "$I_2$". As a consequence, the latter differences could be mistakenly judged as "the injection of the X-ray contrast medium". That is, practically speaking, such an artifact surely impedes that the helical dynamic scanning could be realized at satisfactory levels in the conventional helical scanning type CT imaging systems.

SUMMARY OF THE INVENTION

The present invention has been made in an attempt to solve the above-described problems, and therefore, has an object to provide a novel helical scanning type CT imaging method/system capable of performing a helical dynamic scanning operation such that a helical scanning operation is repeatedly performed so as to observe medical variations in a biological body in an elapse of time.

Another object of the present invention is to provide a helical dynamic scanning type CT imaging method/system capable of preventing an artifact from a subtraction image.

A further object of the present invention is to provide a helical dynamic scanning type CT imaging system with a simple circuit arrangement.

According to one aspect of the present invention, a computerized tomographic (CT) imaging method comprises the steps of scanning a biological body under medical examination in a helical form by projecting radiation irradiated from a radiation source to the biological body during at least first and second helical scanning periods, while the biological body is translated along a preselected direction. The radiation source is simultaneously relatively moved around the biological body. A radiation angle of the radiation source is detected to produce a radiation angle signal, and position of a couch on which the biological body lies is detected as it chanes during the helical scanning periods. The helical scanning operations are controlled on the basis of the radiation angle signal and the detected couch position in such a manner that helically-moved orbits of the radiation source are identical to each other during the first and second scanning periods.

Furthermore, according to another aspect of the present invention, a computerized tomographic (CT) imaging system comprises a radiation source for producing radiation and helical scanning means for scanning a biological body under medical examination in a helical form during at least first and second helical scanning periods by driving the radiation source to project the radiation to the biological body, while the biological body is translated along a preselected direction and simultaneously the radiation source is relatively moved around the biological body so that the first and second helical scannings are performed over a same location of the biological body.

Angle detecting means is proved for detecting a radiation angle of the radiation source to produce a radiation angle signal. Couch position detecting means is provided for detecting a position of a couch, on which the biological body lies, that continuously changes during the helical scanning periods. Controlling means is provided for controlling the helical scanning means to carry out the helical scanning operation based upon the radiation angle signal and the detected couch position in such a manner that helically-moved orbits of the radiation source are identical to each other during the first and second scanning periods.

BRIEF DESCRIPTION OF THE DRAWINGS

The above-described objects, and other features and also advantages of the CT imaging method/system according to the present invention will be apparent from the following description in conjunction with the accompanying drawings, in which.

DETAILED DESCRIPTION OF THE PREFERRED EMBODIMENTS

DEFINITIONS AND BASIC IDEA

Before describing various preferred embodiment of helical dynamic scanning type CT imaging method/system according to the present invention, definitions and a basic idea of this invention will now be described.

Figure 1:
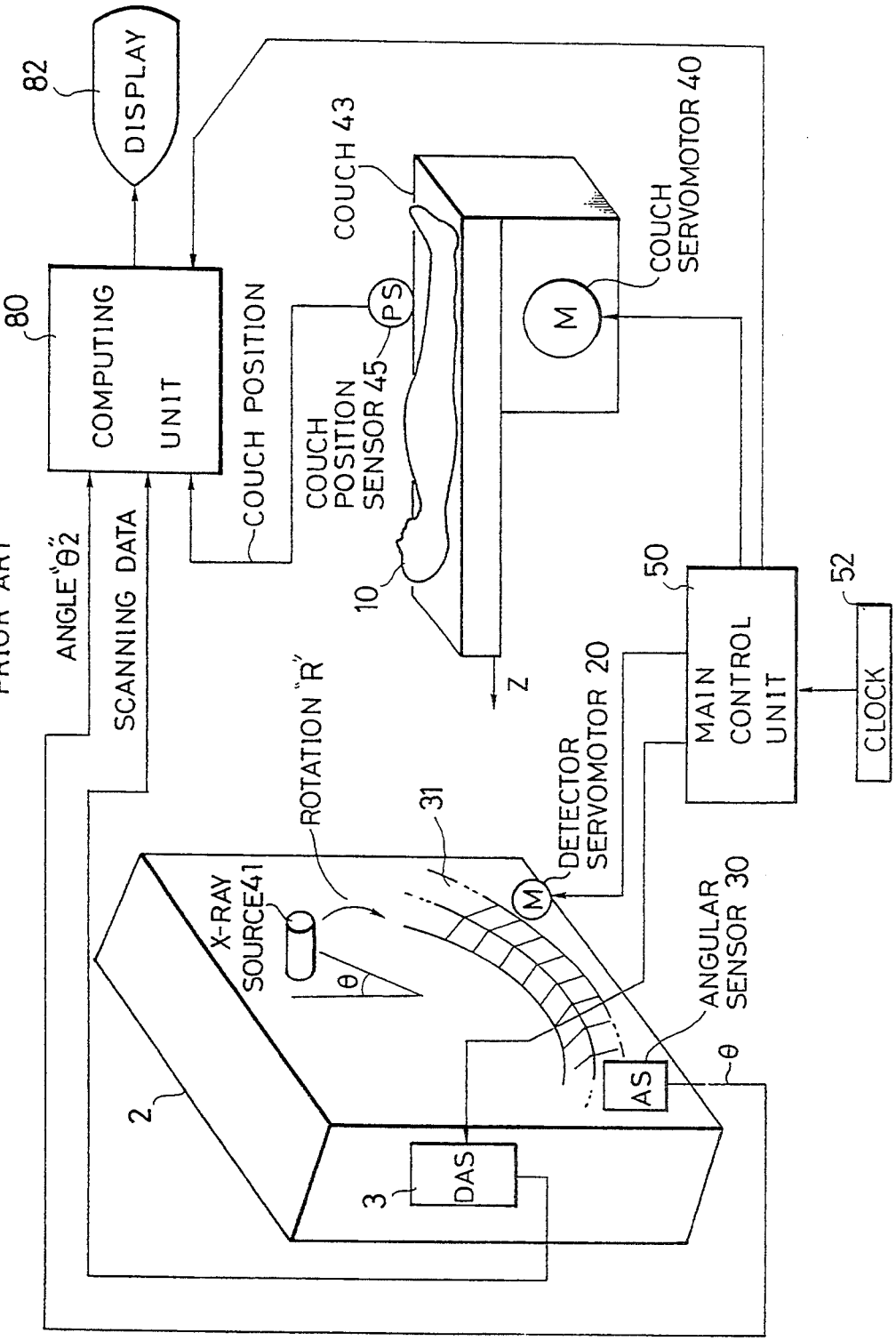
FIG. 1 schematically shows an overall arrangement of the conventional helical scanning type X-ray CT imaging system.
Figure 2A:
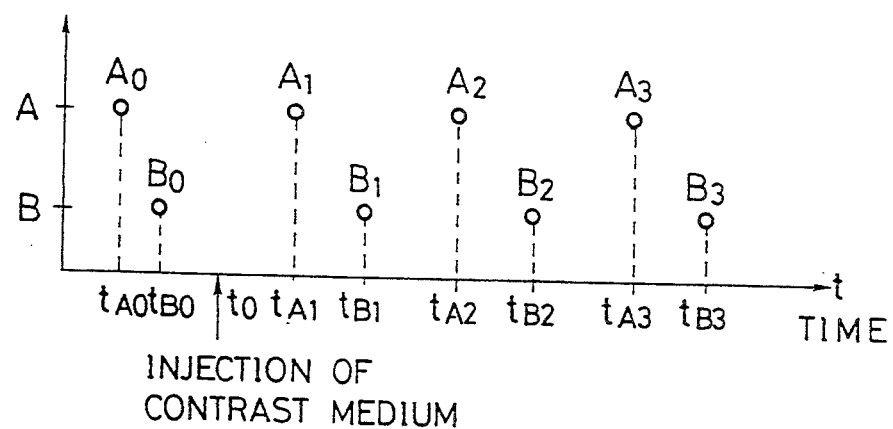
FIGS. 2A and 2B schematically represent helical dynamic scanning operation timing charts effected in the conventional CT imaging system of FIG. 1.
Figure 2B:
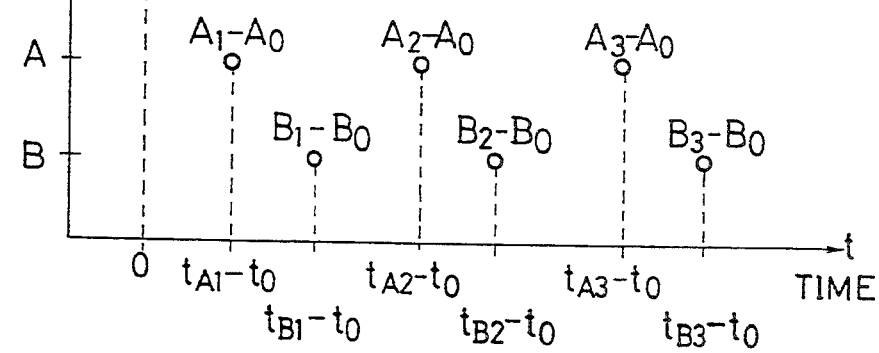
Figure 3A:
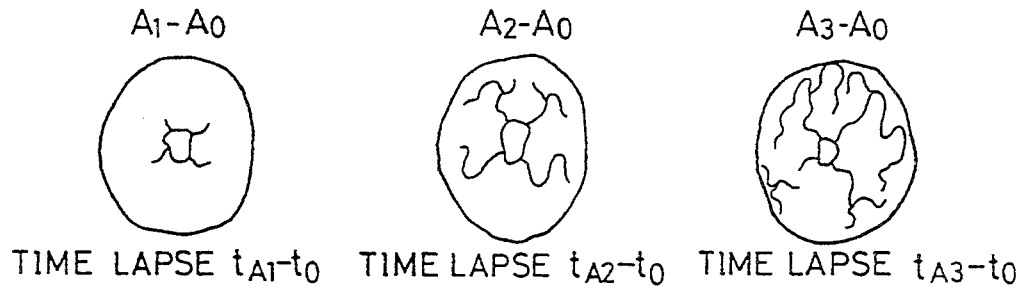
FIGS. 3A and 3B illustrate argiograms and a functional image acquired by the conventional CT imaging system of FIG. 1.
Figure 3B:
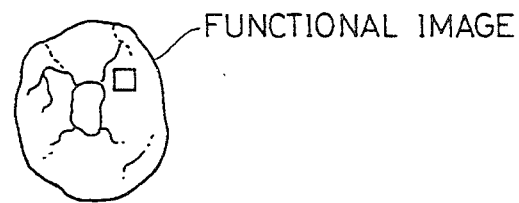
Figure 4:
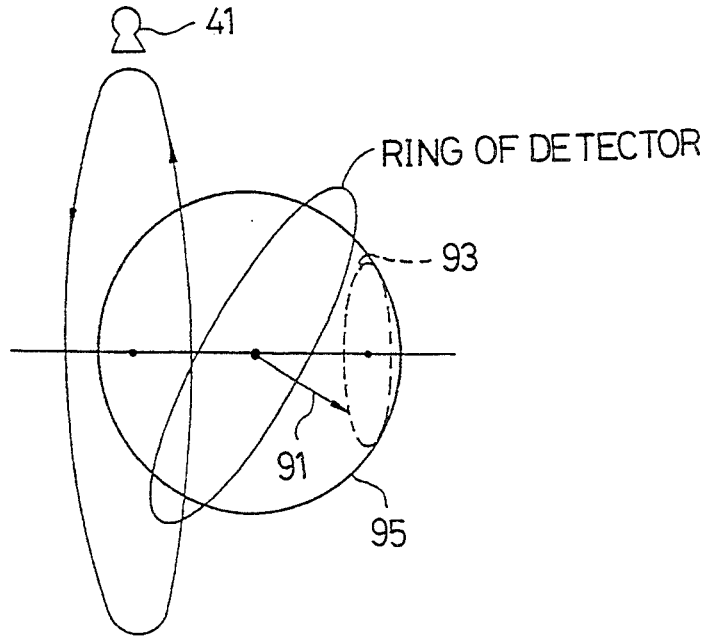
FIG. 4 schematically indicates a detector array of the conventional nutate-rotate type X-ray CT imaging system.
Figure 5:
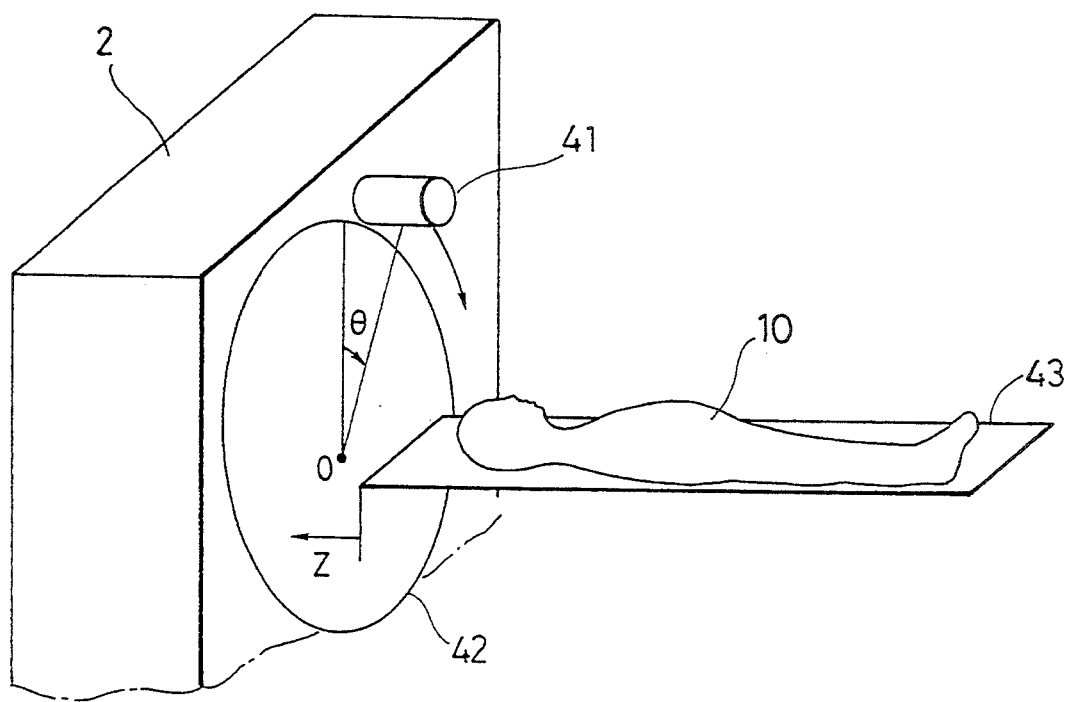
FIG. 5 schematically shows a basic structure of the conventional CT imaging system shown in FIG. 1.
Figure 6:
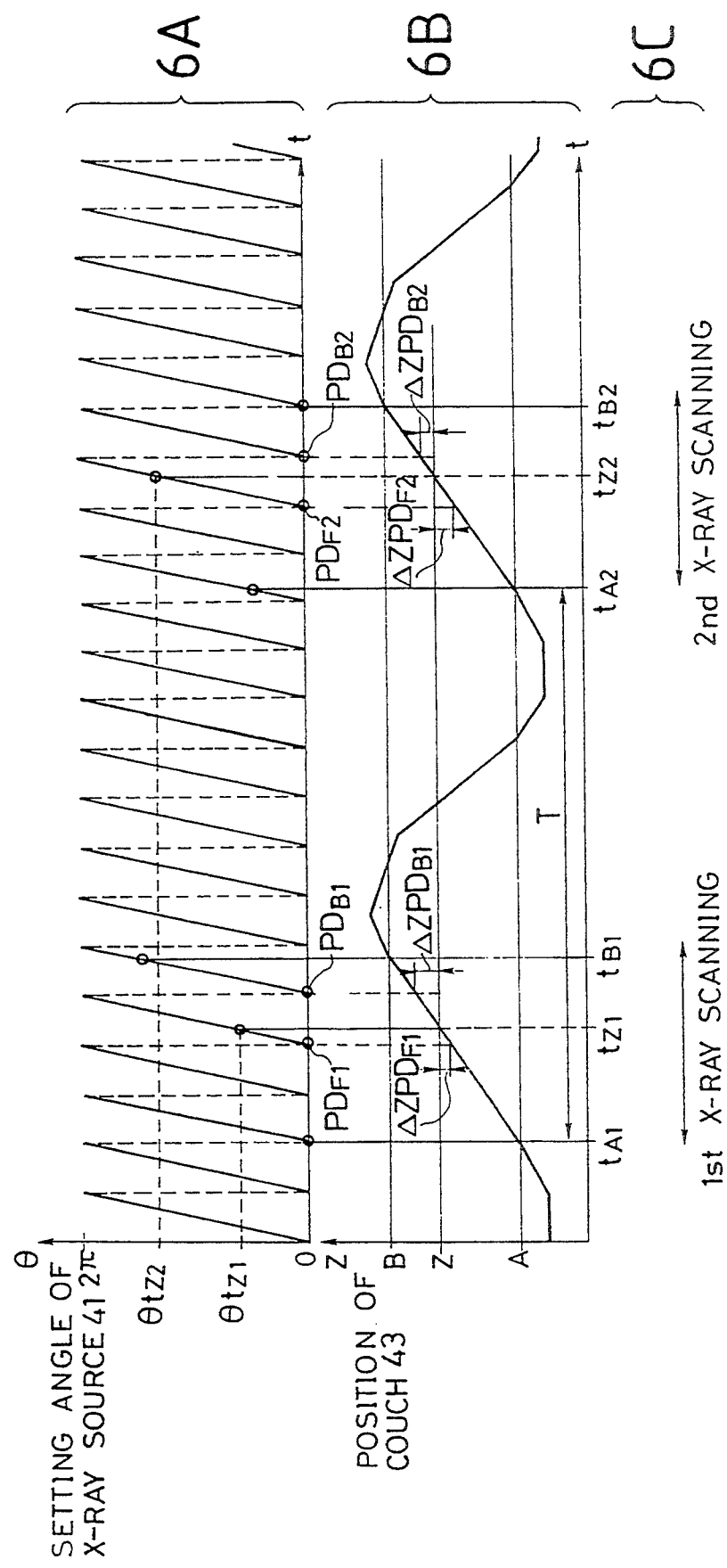
FIGS. 6A, 6B, 6C, and 7 schematically represent the helical dynamic scanning operations performed by the conventional CT imaging system of FIG. 1 and an appearance of artifact.
Figure 7:
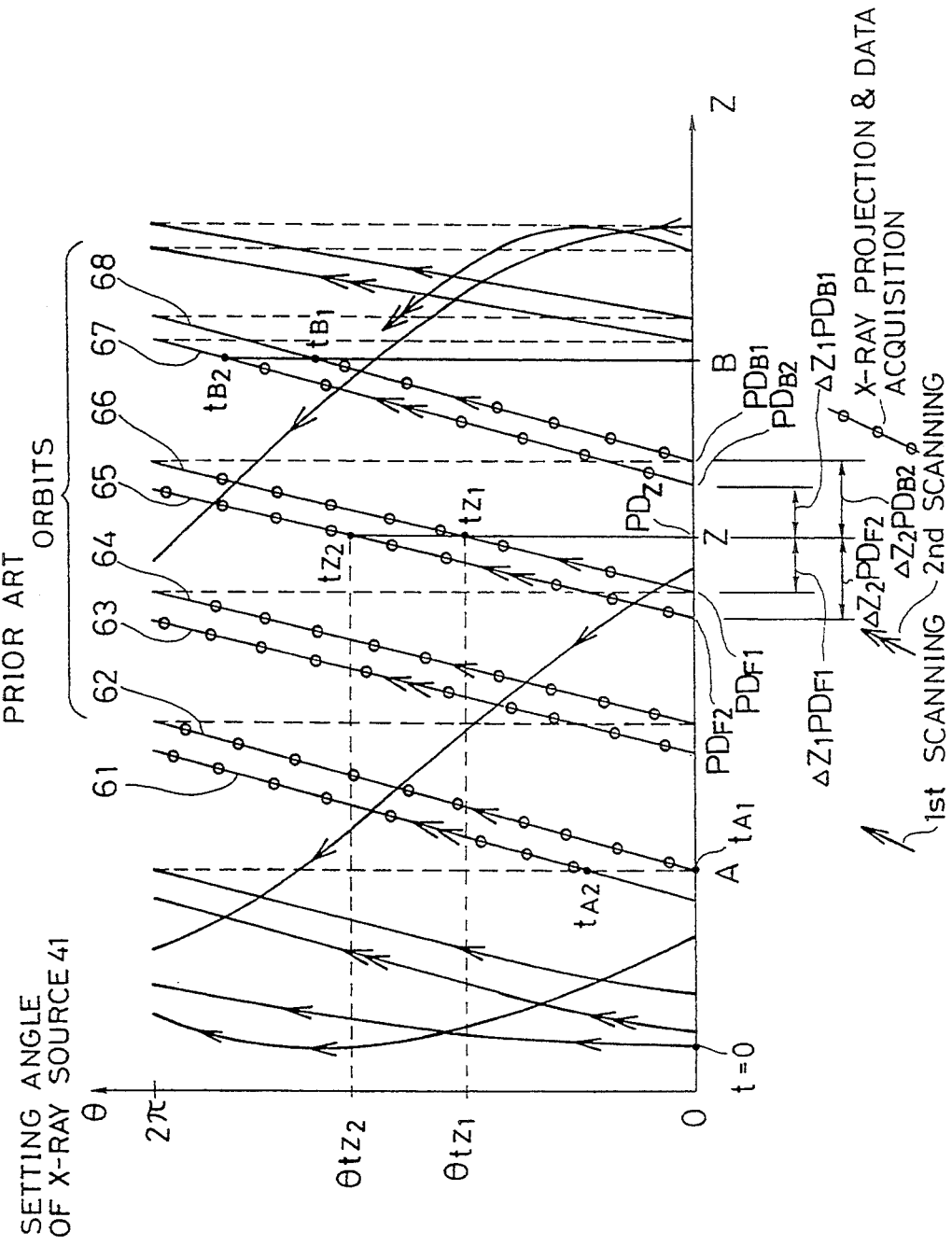

First, a terminology of a "helical scanning" is not limited to the above-described conventional helical scanning type X-ray CT apparatus, as shown in FIG. 1 and/or Mori's U.S. Pat. No. 4,630,202, but should be interpreted as broad as possible. That is to say, while a scanning operation is carried out, a biological body under medical examination is translated, or moved along a preselected direction, whereby a predetermined volume of this biological body can be scanned. This helical scanning operation with broad interpretation may be realized in any one of the known 3rd, 4th and 5th generation X-ray CT imaging systems. In these known X-ray CT imaging systems, an X-ray source may be repeatedly rotated in both of the clockwise direction and the counterclock wise direction, or may be pivoted around a biological body in a rotation range smaller than 360°. In these modified helical scanning operations, orbits of the X-ray source are drawn, like a three-dimensional curve on a cylinder. In a specific case, this curve is partially interrupted. For instance, as illustrated in FIG. 4, a so-called "nutation" is performed in the 4th generation X-ray CT imaging system. A detector array is constructed by arranging a plurality of X-ray detector channels on a plane curve (normally, cylinder). The detector array is spacially neither rotated, nor moved, but nutated. As apparent from the nutation illustration of FIG. 4, assuming now that one end of a normal line vector 91 having a length of 1 is positioned on an origin 92, the other end of this vector 91 is moved while a circule 93 is drawn on a spherical core 95 having a radius of 1 with respect to the origin 92 as a center thereof. Moreover, such a nutation movement is performed in conjunction with another movement of the X-ray tube 41 rotated around the biological body 10 (see FIG. 5). While this X-ray tube 41, is rotated by 360°, the other end of the normal line vector 91 is also rotated by 360° on the circular over the spherical core 95. Such a specific movement may be understood as the "helical" scanning operation according to the present invention.

Moreover, a two-dimensional X-ray detector array may be alternatively employed instead of the above-explained one-dimensional X-ray detector array, and also a plurality of X-ray sources may be employed as this X-ray source 41.

Other than an X-ray tube, a pellet containing a radioisotope irradiating an X-ray may be employed, and many other X-ray generating devices such as an X-ray laser device may be, of course, utilized.

Gamma rays may be employed instead of X-ray pulses. For instance, SPECT (single photon emission CT) systems and PET (positron emission tomography) may be employed with utilizing gamma rays.

In summary, the terminology of "helical scanning (also helical dynamic scanning)" used in this specification should be interpreted as broad as possible in the medical electronics field. Furthermore, the term of "CT scanning system" of the present invention should also cover various types of X-ray CT systems, gamma-ray CT systems and other CT systems.

Then, a basic idea of the present invention is as follows: Simply speaking, both of an X-ray (or equivalent ray) projection angle with respect to a biological body and a couch position are controlled in order to satisfy such a condition that $T/C=$ an integer, where symbol "T" indicates a helical scanning period and symbol "C" denotes a rotation period of an X-ray source. In other words, the X-ray source is continuously moved on the same orbit during a plurality of helical scanning operations, so that the same slice position of the biological body can be repeatedly scanned at the same projection angle during every helical scanning operation (will be referred to a "scanning orbit control" in the helical dynamic scanning operation).

OVERALL ARRANGEMENT OF FIRST HELICAL DYNAMIC SCANNER

For the sake of simple explanation of the present invention and also of easy understanding thereof, a helical dynamic scanning type X-ray CT (computerized tomographic) imaging system will now be described as a first preferred embodiment of the present invention.

Figure 8:
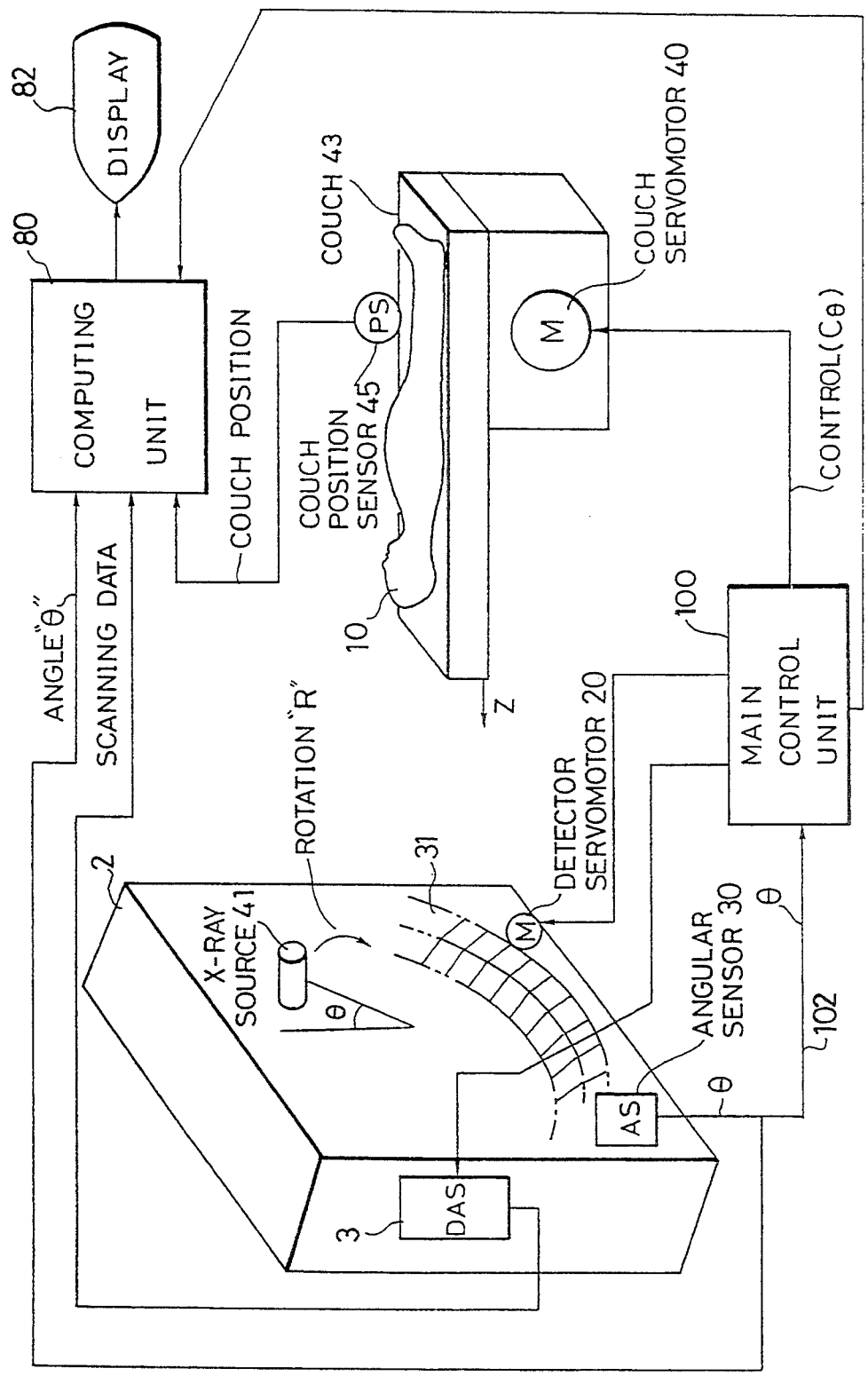
FIG. 8 schematically indicates an overall arrangement of a helical dynamic scanning type X-ray CT imaging system according to a first preferred embodiment of the present invention.

FIG. 8 is a schematic diagram of an overall arrangement of the first helical dynamic scanning type X-ray CT imaging system.

As seen from FIG. 8, most of the structure of the first helical dynamic scanning type X-ray CT imaging system is similar to that of the conventional helical scanning type X-ray CT imaging system indicated in FIG. 1.

FIG. 8, a pair of X-ray source 41 and X-ray detector 31 are positioned within the gantry 2 in such a manner that the X-ray source 41 and the X-ray detector 31 are mutually rotatable and positioned opposite to each other with respect to the biological body 10 under medical examination laid on the couch 43. The couch 43, i.e., the biological body 10 such as a patient is translated along the direction indicated by symbol "Z" (namely, longitudinal direction of the biological body) by driving the couch servomotor 40. A present position of this couch 43 is sensed by the couch position sensor 45.

The X-ray source 41 and the X-ray detector 31 are relatively rotatable by driving the detector servomotor 20 along the rotation direction "R". A rotation angle of this X-ray detector 31 is sensed by an angular sensor 30 to produce angle data "$\theta$". This angle data "$\theta$" is supplied not only to the computing unit 80, but also to a main control unit 100 (will be discussed more in detail).

The data acquisition unit 10 is employed within the gantry 2 to acquire projection data during the helical dynamic scanning operations.

A major featured circuit of this first helical dynamic scanning type X-ray CT imaging system is as follows: The present position of the X-ray source 41 is detected by the angular sensor 30 to produce the angle data "$\theta$" (namely, projection angle of the X-ray source 41). This angle data "$\theta$" is supplied not only to the computing unit 80, but also to the main control unit 100 via a signal line 102. In response to this angle data "$\theta$", the main control unit 100 calculates the above-explained calculation "T/C=an integer" (helical scanning period "T" is divided by rotation period "C") to obtain a couch position control data "$C_\theta$". Then, the couch position control data "$C_\theta$" is supplied to the couch servomotor 40. Upon receipt of such a couch position control data "$C_\theta$", the couch 43 on which the biological body 10 is laid is translated along the Z-direction by the couch servomotor 40 under control of the main control unit 100. As a result, since either the X-ray source 41, or the X-ray detector 31 can be continuously moved along the same orbit during a plurality of helical scanning operations (namely, scanning orbit control in helical dynamic scanning operation), no difference (artifact) is made in the successive X-ray subtraction images (will be described more in detail). Therefore, only such a difference (CT values) that is caused by injection of an X-ray contrast medium can appear in these subtraction images.

SCANNING ORBIT CONTROL BY FIRST HELICAL DYNAMIC SCANNER

As previously described, the major featured operation of the first helical dynamic scanning type X-ray CT imaging system is a so-called "scanning orbit control" during the helical dynamic scanning operation, which will now be described more in detail.

In FIG. 8, it is now assumed that the X-ray source 41 and the X-ray detector 31 are relatively rotated at a constant angular velocity by the detector servomotor 20, and a present position of this X-ray source 41 is sensed by the angular sensor 30 as an angle "$\theta$".

Figure 9:
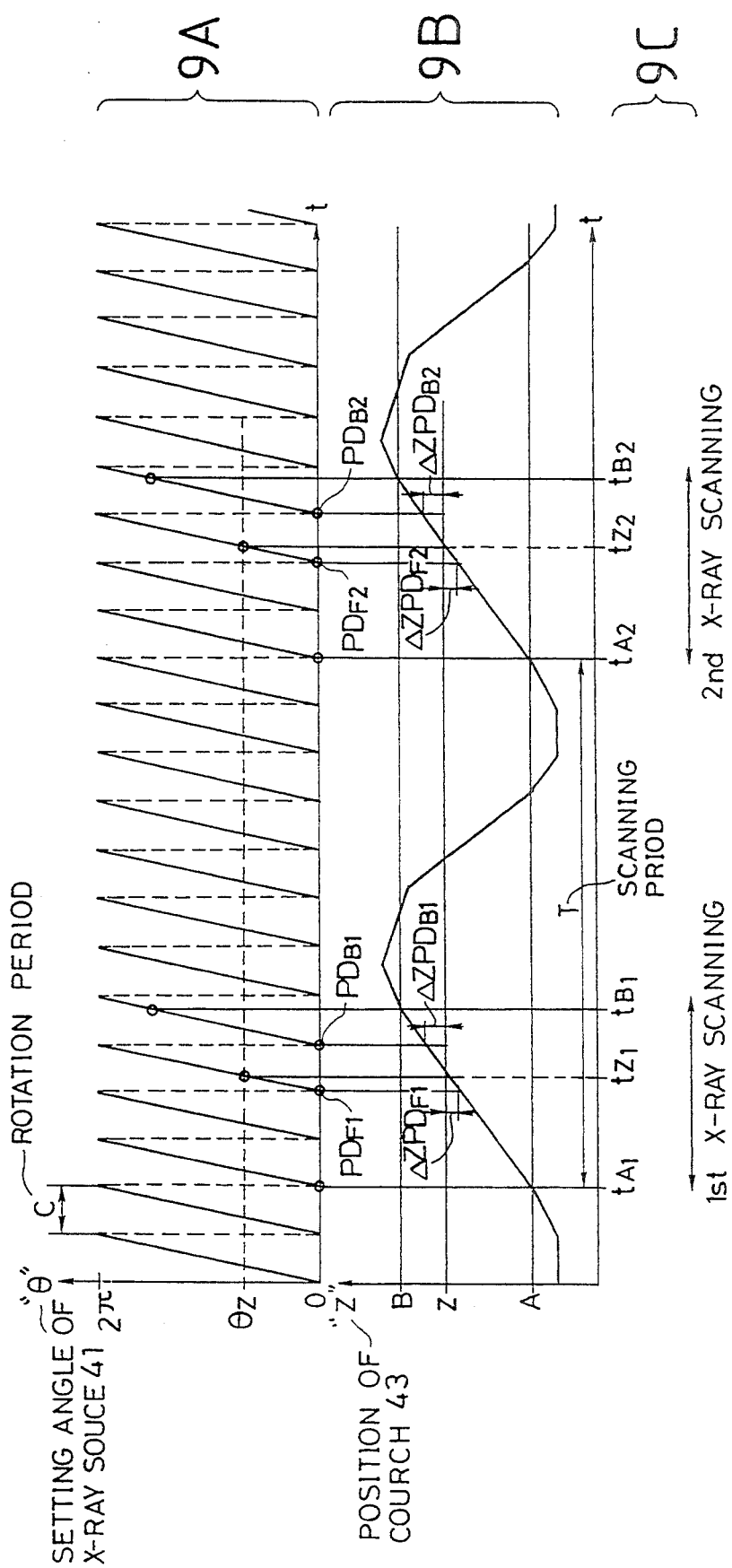
FIGS. 9 (comprised of 9A, 9B and 9C) and 10 schematically represent a helical dynamic scanning operation performed by the X-ray CT imaging system of FIG. 8.

A relationship between this angle "$\theta$" and an elapse of time "t" is represented in FIG. 9A. The couch 43 is continuously translated, or moved along the Z-direction. Another relationship between the present position of the couch 43 and an elapse of time "t" is shown in FIG. 9B. In FIG. 9B, a range defined by $A \leq z < B$ corresponds to an imaging range during which X-ray pulses are projected from the X-ray source 41 and penetrated through a predetermined slice portion of the biological body 10, and thereafter detected by the X-ray detector 31. It should be noted that this imaging range is also defined by the scanning period "T" = $|t_{A2} - t_{A1}|$, during which the translation speed of the couch 43 remains constant.

As previously described, the main control unit 100 controls the present position "z" of the couch 43 and the present angle "$\theta$" of the X-ray source 41 in such a manner that the projection angle "$\theta$" of the X-ray source 41 at the position "z" of the couch 43 always has the same value during a repetition of the helical scanning operation. To this end, the main control unit 100 controls both of the present position "z" of the couch 43 and the angle "$\theta$" of the X-ray source 41 (or X-ray detector 31) in such a manner that:

$$T/C = \text{any integer} \tag{1}$$

where symbol "T" denotes the scanning period (= "$t_{A2} - t_{A1}$"), and symbol "C" shows the rotation period (see FIG. 9A). As a consequence, the X-ray source 41 can be continuously move along the same orbit during such a helical dynamic scanning operation.

In a concrete example, this main control unit 100 controls both of the couch position "z" and the X-ray source position "$\theta$" in order to satisfy the bellow-mentioned conditions I, II, III.

CONTROL CONDITIONS (I) The translation speed of the couch 41 during acquisition of the X-ray projection data should be constant. In other words, the translation speed during the time period of "$t_{A1}$" to "$t_{B1}$" (i.e., first helical scanning), and the translation speed during the time period of "$t_{A2}$" to "$t_{B2}$" (i.e., second helical scanning) should be constant, and also be equal to each other. Similarly, this speed condition is applied to other speed controls after the third helical scanning.

(II) The angular velocity of the X-ray source 41 should be constant, as illustrated in region FIG. 9A, and the rotation period is defined as "C".

(III) Assuming now that the scanning period "T" is defined as "$t_{An-1} - t_{An}$", this scanning period "T" should be made greater than the rotation period "C" by any integer, where symbol "$t_{An}$" indicates a starting time instant for an n-th helical scanning, and symbol "$t_{An-1}$" denotes a starting time instant for an (n−1)th helical scanning.

Figure 10:
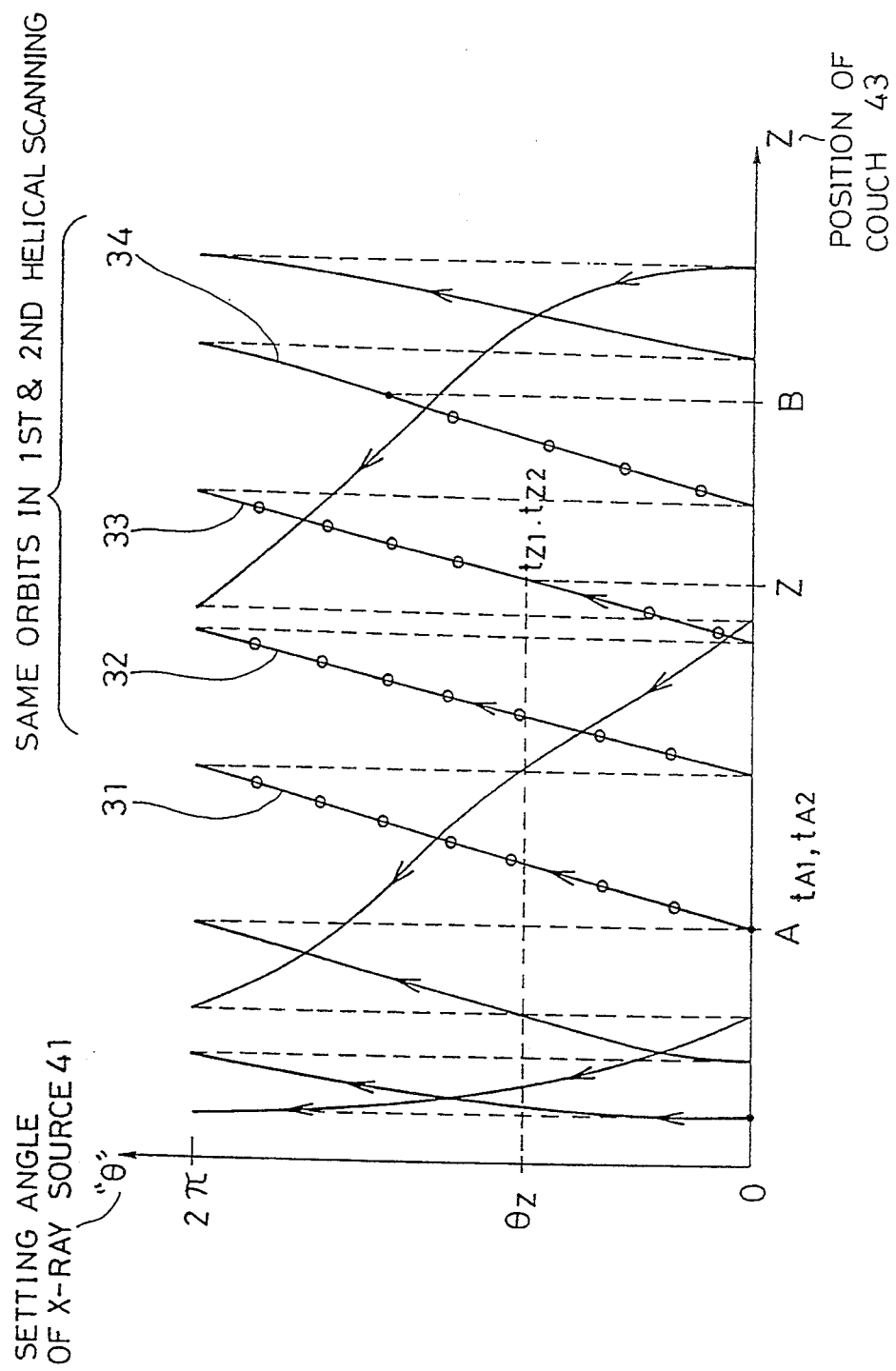

Since the above-described three conditions are satisfied during the scanning orbit control, the X-ray source 41 can be continuously moved along the same orbits 31 to 34 shown in FIG. 10 during the first and second helical scanning operations, resulting in no artifact in the subtraction image.

It should be noted that as shown in FIGS. 9B and 9C, one scanning period "T" is constructed of at least one data acquisition period ("$t_{A1}$" to "$t_{B1}$") and one returning period to a home position of the couch 43. Also, an X-ray contrast medium is injected at an interval between the first helical scanning operation and the second helical scanning operation in order to acquire angiogram data.

CEREBRAL BLOOD VOLUME MEASUREMENT BY SECOND HELICAL DYNAMIC SCANNER

Figure 11:
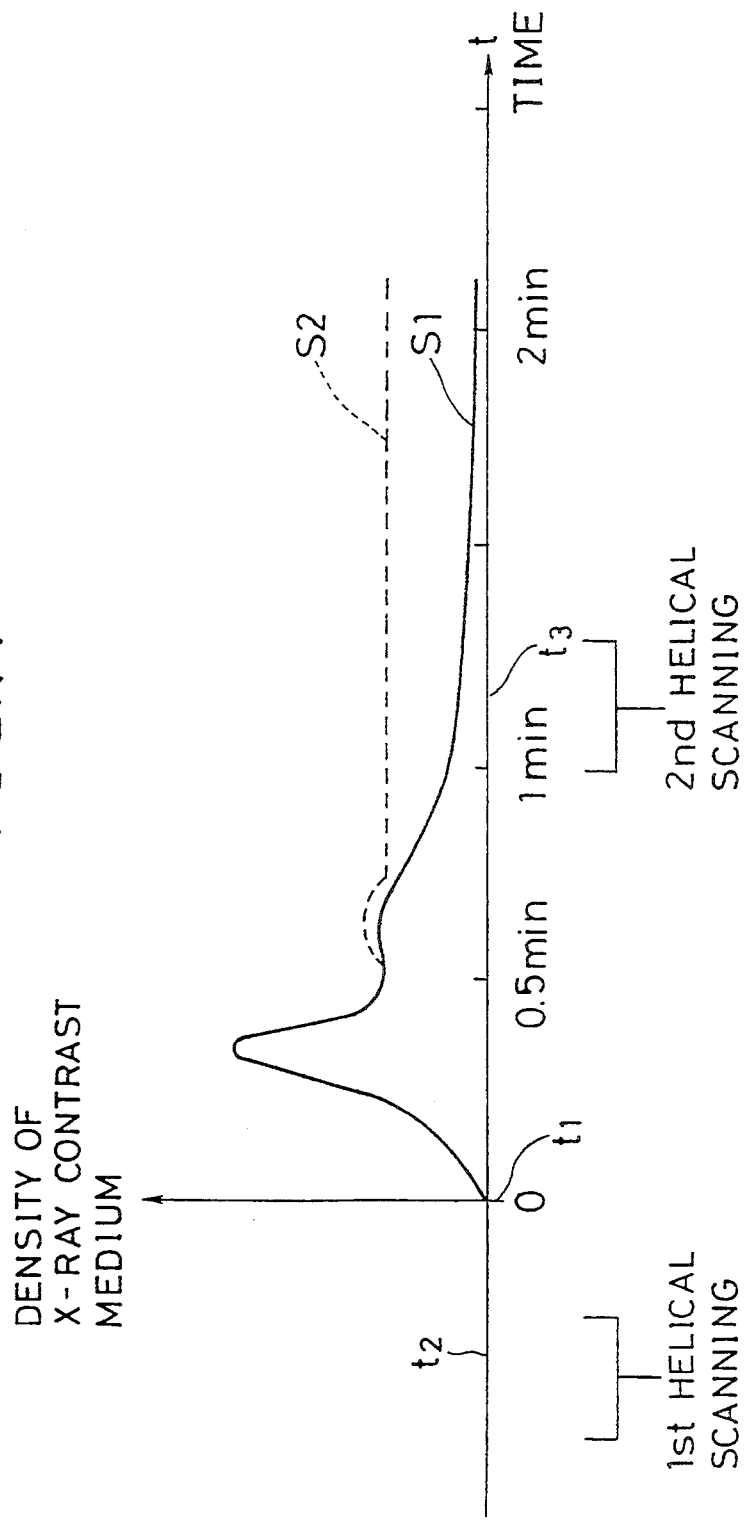
FIG. 11 shows a characteristic curve of CBV measurement according to a second preferred embodiment of the present invention.
Figure 12:
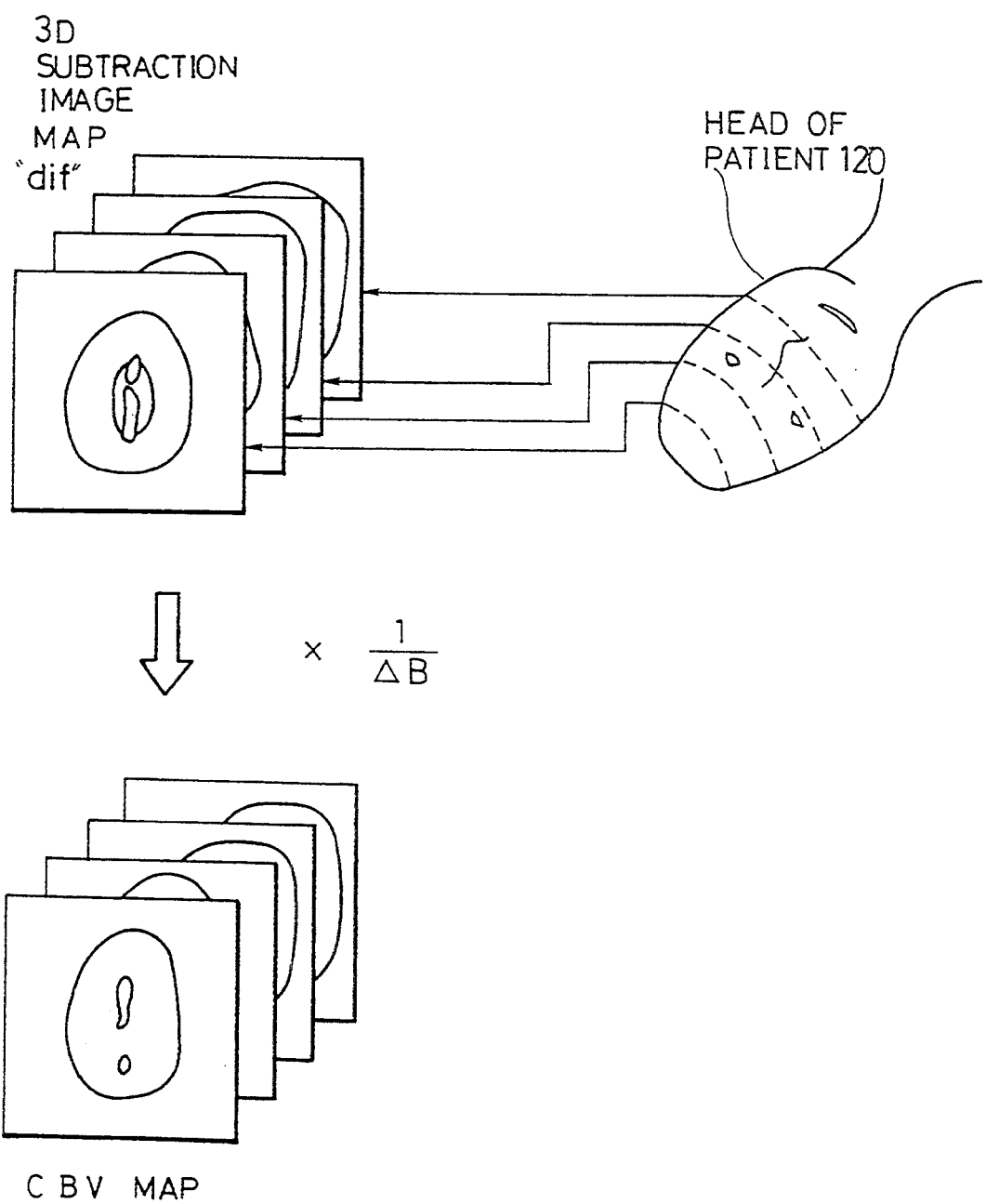
FIG. 12 schematically indicates the CBV measuring operation according to the second preferred embodiment.

Referring now to FIGS. 11 and 12, a cevebral blood volume measurement of a three-dimensional tissue in a patient 120, carried out by the helical dynamic scanning type CT imaging apparatus according to a second preferred embodiment of the present invention, will be described. That is, this cevebral blood volume measurement may be carried out by the second helical dynamic scanning type CT imaging system (not shown in detail) which is identical to the first helical dynamic scanning type X-ray CT imaging system shown in FIG. 8.

In general, a flood flow distribution of a brain of a biological body is so-called CBV (Cevebral blood Volume), which can provide various medical information about diagnostic and curing data of this biological body. As the conventional CBV measuring method, there have been proposed to utilize SPECT and PET. In these CBV-measurement SPECT and PET, a radioisotope combined with a predetermined medicine not leaked from blood vessels is injected into a blood vessel of the brain, and 3-dimensional images of the brain are acquired to grasp an RI distribution. Then, if an amount of R.I. (radioisotope) contained in a unit volume of blood is measured, then CBV of the brain can be obtained.

However, these conventional CBV measurements with employment of SPECT and PET have the following drawbacks. That is, a very expensive medicine must be used, a lengthy measuring time is required, and a specific RI handling apparatus must be employed. Nevertheless, the resultant space resolution is rather low, e.g., 2 to 5 mm.

There is another conventional CBV measuring method in which several slice portions of a brain are measured by way of the conventional X-ray CT apparatus, while injecting such an X-ray contrast medium as a non-ionized iodine contrast medium into a brain vessel. The CBV can be measured by checking variations in CT values before and after injection of the X-ray contrast medium.

However, similar to the above conventional CBV measurement, this conventional CBV measurement has such drawbacks that the CBV can be measured only in a limited number of slice portions, and a length measurement time is necessarily required.

To avoid these drawbacks of the conventional CBV measuring methods, a very unique CBV measurement can be achieved by employing the helical dynamic scanning type X-ray CT imaging system as shown in FIG. 8 in accordance with the second preferred embodiment of the present invention. In summary, the helical dynamic scanning operation is carried out with respect to, for instance, a brain of a patient 120 (see FIG. 12) to acquire X-ray projection images thereof. Subsequently, a series of subtraction image "dif" is calculated in the computing unit 80, so that desirable CBV may be measured in the three-dimensional way.

FIG. 11 represents a characteristic diagram indicative of variations contained in density (CT values) after the X-ray contrast medium has been injected at a time instant "$t_1$". In this characteristic diagram, a curve "$S_1$" indicates a density variation curve with no X-ray contrast medium, whereas a curve "$S_2$" shows a density variation curve with the X-ray contrast medium.

A CBV measuring procedure according to the second preferred embodiment is carried out as follows:

At a time instant "$t_2$" before the X-ray contrast medium is injected at the above time instant "$t_1$", a first helical dynamic scanning operation of the brain of the patient 120 is performed to acquire CT image data (referred to "pre-DATA"). Then, at the time instant "$t_1$", the X-ray contrast medium is injected into the blood vessel in this brain, and then starts to be flown into this blood vessel.

After approximately 1 minute has passed, this contrast medium is distributed into the whole blood vessel in a substantially uniform state. At the same time, this injected X-ray contrast medium is successively ejected from a kidney of the patient 120. At this time, a second helical dynamic scanning operation is performed under such a condition that the X-ray source 41 is moved along the same orbit during the first helical dynamic scanning operation under control of the main control unit 120 (see FIG. 8). As a result, CT image data (referred to "post-DATA" is acquired.

Then, the pre-DATA (CT image data) is subtracted from the post-DATA (CT image data) to obtain such a three-dimensional contrast medium distribution, as a subtraction image map "dif", as shown in FIG. 12.

Since this subtract image map "dif" corresponds to variation amount of the CT value, this variation amount is converted into an amount of blood "CBV" in accordance with the following calculation method.

$$CBV = dif/\Delta B \quad (2)$$

$$\Delta B = (Bpost - Bpre) \quad (3).$$

where symbol "Bpost" denotes a CT value of the blood acquired before injection of the X-ray contrast medium, and symbol "Bpre" shows a CT value of the blood after injection of the X-ray contrast medium.

There are three typical methods to obtain "$\Delta B$".

(B-1) When the blood is collected at the time instants "$t_2$" and "$t_3$" (see FIG. 11), the CT values of this blood are measured by operating the second helical dynamic scanner, and a difference between these CT values is calculated as "$\Delta B$".

(B-2) At the time instant "$t_3$", the blood is collected and then processed by the chemical analysis so as to obtain density of the X-ray contrast medium contained therein. This density is converted into a variation amount of a CT value.

(B-3) No blood collection is carried out. Alternatively, a measurement is carried out for $\Delta CT$ value of a large blood vessel contained in the subtraction image map "dif".

As described above, according to the second preferred embodiment, the CBV of the brain of the patient 120 can be measured in a similar helical dynamic scanning operation of the first X-ray CT imaging system shown in FIG. 8. As a consequene, high special resolution can be achieved without requiring lengthy measurement time. Moreover, no careful attention is required to handle R.I. Inexpensive medicine can be utilized. Since the helical dynamic scanning operation can be completed within a short time, there is no adverse influence caused by movements of the patient 120, so that CBV results can be improved. Then, three-dimensional blood distribution within the brain can be observed.

What is claimed is:

1. A computerized tomographic (CT) imaging method comprising the steps of:
    scanning a biological body under medical examination in a helical form by projecting radiation irradiated from a radiation source to said biological body during at least first and second helical scanning periods, while said biological body is translated along a preselected direction and simultaneously said radiation source is relatively moved around said biological body, so that the first and second helical scannings are performed over a same location of the biological body;
    detecting a radiation angle of said radiation source to produce a radiation angle signal;
    detecting a position of a couch, on which the biological body lies, that continuously changes during the helical scanning periods; and
    controlling helical scanning operations based upon said radiation angle signal and the detected couch position in such a manner that helically-moved orbits of said radiation source are identical to each other during said first and second scanning periods.

2. A computerized tomographic imaging method as claimed in claim 1, wherein said helical-scanning-operation controlling step is carried out based upon the following condition:

$T/C =$ an integer, where symbol "T" denotes a scanning period of said one of the first and second helical scanning operations, and symbol "C" indicates a moving period of said radiation source.

3. A computerized tomographic imaging method as claimed in claim 1, wherein said radiation source is an X-ray tube, whereby X-ray projection image data of the helically scanned biological body is acquired.

4. A computerized tomographic imaging method as claimed in claim 3, further comprising the steps of:
  calculating a variation contained in CT values by subtracting the successively acquired X-ray projection images; and
  converting said variation in the CT values into a cerebral blood volume (CBV) of the helically scanned biological body.

5. A CT imaging system comprising:
  a radiation source for producing radiation;
  helical scanning means for scanning a biological body under medical examination in a helical form during at least first and second helical scanning periods by driving said radiation source to project the radiation to said biological body, while said biological body is translated along a preselected direction and simultaneously said radiation source is relatively moved around said biological body, so that the first and second helical scannings are performed over a same location of the biological body;
  angle detecting means for detecting a radiation angle of said radiation source to produce a radiation angle signal;
  couch-position detecting means for detecting a position of a couch, on which the biological body lies, that continuously changes during the helical scanning periods; and
  controlling means for controlling said helical scanning means to carry out the helical scanning operation based upon the radiation angle signal and the couch position detected by the couch-position detecting means in such a manner that helically-moved orbits of said radiation source are identical to each other during said first and second scanning periods.

6. A CT imaging system as claimed in claim 5, wherein said controlling means performs said helical scanning process based on the following condition:

$T/C =$ an integer, where symbol "T" denotes a scanning period of said one of the first and second helical scanning operations, and symbol "C" indicates a moving period of said radiation source.

7. A CT imaging system as claimed in claim 5, wherein said radiation source is an X-ray tube, whereby X-ray projection image data of the helically scanned biological body is acquired.

8. A CT imaging system as claimed in claim 7, further comprising:
  means for calculating a variation contained in a CT values by subtracting the successively acquired X-ray projection images; and
  means for converting said variation of the CT values into a cevebral blood volume (CBV) of the helically scanned biological body.

* * * * *